United States Patent [19]
Barels et al.

[11] Patent Number: 5,747,005
[45] Date of Patent: May 5, 1998

[54] OIL-BASED, ANTI-PLAQUE DENTIFRICE COMPOSITION

[76] Inventors: Ronald R. Barels, 2856 E. Washington Ave., Escondido, Calif. 92027-1822; Charles M. Cohler, 18776 Bernardo Trails Dr., San Diego, Calif. 92128

[21] Appl. No.: 510,420

[22] Filed: Aug. 2, 1995

[51] Int. Cl.$^6$ .......................... A61K 7/28; A61K 33/04; A61K 33/30; A61K 31/355
[52] U.S. Cl. .................. 424/50; 424/49; 424/541; 424/642; 424/643; 424/702; 514/458
[58] Field of Search ................. 424/49–88, 641, 424/642, 643, 702; 514/458

[56] References Cited

U.S. PATENT DOCUMENTS

| | | |
|---|---|---|
| Re. 32,672 | 5/1988 | Huth et al. |
| 1,460,179 | 6/1923 | Ruthkrauff. |
| 3,562,385 | 2/1971 | Block et al. |
| 3,574,824 | 4/1971 | Echeandia et al. |
| 3,590,121 | 6/1971 | Schiff et al. |
| 3,622,661 | 11/1971 | King et al. |
| 3,630,924 | 12/1971 | Miller. |
| 3,910,296 | 10/1975 | Karageozian et al. |
| 4,003,971 | 1/1977 | Mannara. |
| 4,022,886 | 5/1977 | Vinson et al. |
| 4,069,311 | 1/1978 | Mannara. |
| 4,069,312 | 1/1978 | Mannara. |
| 4,082,841 | 4/1978 | Pader. |
| 4,152,418 | 5/1979 | Pader. |
| 4,154,815 | 5/1979 | Pader. |
| 4,269,822 | 5/1981 | Pellico et al. |
| 4,292,304 | 9/1981 | Barels et al. |
| 4,355,022 | 10/1982 | Rabussay. |
| 4,411,885 | 10/1983 | Barels et al. |
| 4,537,764 | 8/1985 | Pellico et al. |
| 4,564,519 | 1/1986 | Pellico et al. |
| 4,578,265 | 3/1986 | Pellico et al. |
| 4,693,888 | 9/1987 | Miyahara et al. |
| 4,725,428 | 2/1988 | Miyahara et al. |
| 4,826,675 | 5/1989 | Gaffar et al. |
| 4,986,981 | 1/1991 | Glace et al. |
| 4,988,500 | 1/1991 | Hunter et al. |
| 5,000,939 | 3/1991 | Dring et al. |
| 5,085,851 | 2/1992 | Okada et al. |
| 5,242,693 | 9/1993 | Kurihara et al. |

*Primary Examiner*—Shep K. Rose
*Attorney, Agent, or Firm*—Majestic, Parsons, Siebert & Hsue

[57] ABSTRACT

The present invention provides an oil-based, anti-plaque dentifrice comprising vitamin E and an enzyme in an admixture which is effective to dissolve plaque and to resist plaque formation. The preferred dentifrice composition is substantially anhydrous, and includes a chelating agent and a promoter to assist the enzyme in fighting plaque.

14 Claims, No Drawings

OIL-BASED, ANTI-PLAQUE DENTIFRICE COMPOSITION

FIELD OF THE INVENTION

The present invention generally relates to a vitamin E oil-based dentifrice and more particularly, to an enzymatic vitamin E oil-based dentifrice which is effective in reducing plaque and resisting plaque formation in an oral cavity.

BACKGROUND OF THE INVENTION

Oral plaque is responsible for both dental caries and periodontal disease, both of which remain quite pervasive in the human population. Plaque is a mucopolysaccharide which forms naturally in the mouth, as a result of the presence of saliva and bacteria. At the outset of plaque formation, plaque exists as a web of soft, sticky gelatin, called the pellicle. The pellicle provides a haven for the lodging and multiplication of bacteria. Thus, within a very short time, plaque becomes predominantly bacterial.

A variety of compositions have been developed to attack the bacterial portion of plaque. For example, U.S. Pat. No. 4,335,022, issued Oct. 19, 1982 to Rabussay, describes a hydrous, enzymatic dental treatment composition used to destroy certain types of cariogenic bacteria via hydrolysis. However, enzymes are known to become unstable and to lose activity in the presence of water or moisture, rendering such hydrous enzymatic compositions both unstable and ineffective.

Anhydrous toothpastes including an oil component and enzymatic additives are known, as exemplified by U.S. Pat. No. 3,574,824, issued Apr. 13, 1971 to Echeandia et al. Among the disadvantages of such prior known anhydrous oil-based toothpastes are an unpleasant mouth feel or oily sensation when used, and a reduced shelf life as compared to conventional, hydrous toothpastes due to the tendency of the oil component to oxidize and to become rancid. Additionally, these toothpastes are not optimal anti-plaque compositions, as the enzyme additive is rapidly diluted in the mouth and thus, is washed away from the tooth or gum area before it can be effective in fighting oral plaque.

U.S. Pat. No. 4,411,885, issued Oct. 25, 1983 to Barels et al., discloses an encapsulated or tableted oil-based dentifrice, including a source of vitamin E. The vitamin E component of the dentifrice is present in a quantity sufficient to reduce or to eliminate the unpleasant mouth feel or oily sensation associated with the previously known anhydrous oil-based toothpastes. The vitamin E also tends to reduce oxidation of the oil base and thus, to improve the shelf life of the dentifrice. While this encapsulated or tableted dentifrice eliminates many of the disadvantages of earlier dentifrices, it employs an abrasive agent, rather than an enzyme additive, to fight oral plaque.

SUMMARY OF THE INVENTION

It is an object of the present invention to provide an oil-based, anti-plaque dentifrice, which is effective to reduce plaque and to resist plaque formation.

This and other objects and advantages are provided in one aspect of the present invention by an oil-based, anti-plaque composition for use in an oral cavity in the form of a localizing admixture. This localizing admixture must include vitamin E and at least one enzyme selected from proteases, lipases and saccharinases. The vitamin E and the selected enzyme form the localizing admixture that maintains the enzyme in close approximation to the tooth, periodontium, or other oral substrate for a sufficient period for effective enzymatic activity. Thus, the admixture prevents enzyme dilution in these plaque-prone areas and facilitates effective anti-plaque activity, as the enzymes attack the proximal initial soft gelatin, or pellicle formation, before bacteria become attached and concentrated. Further, the vitamin E interacts with saliva in the mouth to form a thin coating on the tooth, periodontium, or other oral substrate which serves as a prophylaxis against plaque formation for a period following the use of the composition.

Preferred embodiments are substantially anhydrous.

Use of the inventive composition results in dramatically improved oral health of its users. Examination and testing of dental patients using the inventive composition showed striking improvements in the gingival and dental health of the patients. Further, patients treated with the inventive composition showed an almost complete lack of dental plaque, unlike patients simply treated with a vitamin E-containing composition. Such evidence shows the inventive composition to be more effective as an anti-plaque dentifrice than a composition including vitamin E alone.

Additional objects, advantages and features of the various aspects of the present invention will become apparent from the following description of its preferred embodiments.

DESCRIPTION OF PREFERRED EMBODIMENTS

The present invention is an oil-based composition which enzymatically reduces or eliminates initial plaque formation on a tooth, periodontium (gingivae or gums) or other plaque-vulnerable substrate and reduces the occurrence of dental caries and periodontal disease. The composition is particularly effective in localizing and maintaining its enzyme component close to a plaque-prone substrate, thereby facilitating effective plaque-fighting enzymatic activity at the likely site of plaque formation.

The inventive composition includes vitamin E and at least one enzyme which form an admixture, which is characterized as being of a "localizing" nature or consistency with respect to the substrate being treated. By "localizing", it is meant that the admixture is of sufficient nature or consistency such that when it is placed in contact with a tooth, periodontium, or other plaque-vulnerable oral substrate, the vitamin E component localizes or maintains the enzyme component in close approximation to the substrate for a period sufficient for the enzyme to act on the initial pellicle formation, thereby breaking down and reducing or eliminating the plaque on the substrate. This period preferably encompasses the range of tooth-brushing times typically employed by users, on the order of about 30 seconds to about 3 minutes, and most preferably approaches about 3 minutes. Thus, the enzyme is not prematurely diluted or washed away from the substrate by saliva, but is maintained in sufficient proximity of the substrate for effective enzymatic action. The localizing admixture of the inventive composition thus provides an effective enzyme delivery system for treating plaque-prone areas in an oral cavity.

The inventive composition is oil-based, with the oil base comprising at least about 10 weight percent of the dentifrice composition. More preferably, the oil base is the major component of the dentifrice composition and is, effectively, the sole vehicle, as the inventive composition is preferably substantially anhydrous. The anhydrous form of the inventive enzymatic composition is preferred because enzymes are known to be compromised in terms of stability and activity in the presence of water or moisture. Thus, the anhydrous composition has a greater shelf life than its hydrous counterpart. The oil base is most preferably from about 55 weight percent to about 70 weight percent of the total composition.

The oil-based composition must include vitamin E. Various advantages attributed to vitamin E have been described in the above-mentioned U.S. Pat. No. 4,411,885, which is incorporated herein in its entirety by this reference. For example, the vitamin E component of the dentifrice composition substantially reduces or eliminates the oily sensation, or unpleasant mouth feel, of the oil base and tends to reduce oxidation of the oil base. This is particularly important where the oil base constitutes the major component of the dentifrice composition.

Additionally, it is believed that inclusion of vitamin E assists in providing beneficial oral health of the tissues adjacent a user's teeth, usually in conjunction with the removal of plaque by means such as a toothbrush, dental floss or the like. That is, it is believed that the inclusion of a sufficient source of vitamin E in the oil base is of assistance as part of an oral health program for users with gingival irritations, and may be useful following oral surgery, or for users, with incipient gum deterioration.

In the present invention, it has been discovered that the vitamin E component of the dentifrice composition, when mixed sufficiently with the enzyme, additionally functions to hold the enzyme in close proximity to the oral substrate and thus, to the plaque formation on the substrate. Thus, by reducing or preventing rapid enzyme dilution or wash-out in the oral cavity, the admixed vitamin E facilitates enzymatic dissolution of the plaque formation.

Further, it has been discovered that the vitamin E component, when combined with saliva, forms a thin coating or film on the oral substrate. This coating or film acts as a prophylaxis which reduces or prevents new plaque formation for a period after use of the dentifrice composition.

Thus, the inventive composition serves as an effective enzyme delivery system, an effective enzymatic composition for reducing plaque, and a prophylaxis with respect to plaque formation after use.

Vitamin E (also known as alpha-tocopherol) in either the acetate (alphatocopheryl acetate) or the succinate (alphatocopheryl succinate) form can be used to form both an effective enzyme delivery system and an anti-plaque prophylactic coating. Vitamin E in either of these forms is sufficient in the composition to hold the enzyme in sufficient proximity to the oral substrate for effective enzymatic action on local plaque, and to combine with saliva to form the plaque-preventive coating on the substrate.

An international unit of vitamin E is generally considered to be equal to 1 milligram of standard DL-alphatocopheryl acetate. Although vitamin E is present in very small concentration (1.0–0.3%) in wheat germ, corn, sunflower seed, rape seed, and soybean oil, a use of such oils, by themselves, does not result in an amount of vitamin E sufficient for providing an effective enzyme delivery system. Thus, vitamin E neat is preferably used as the oil base, in the amounts previously described for the oil base, to provide a sufficient amount of vitamin E in the oil-based dentifrice composition.

In the inventive composition, the vitamin E is admixed with an enzyme, which is a protease, a lipase or a saccharinase, or a combination of such enzymes. The enzymes are chosen based on their effectiveness at the pH of the oral cavity and in combining to break down and to eliminate the components of dental plaque. The enzymes may be neutral, acidic or alkaline and may be derived from any plant or animal source, including microbial sources. Preferably, the enzymes are derived from pancreatin, trypsin, papain, collagenase, keratinase, carboxylase, aminopeptidase, lactate dehydrogenase and glucosyltransferase, and most preferably, from pancreatin and papain.

An effective composition is provided when the vitamin E and the enzyme component form an admixture in which the vitamin E and the enzyme are in a weight ratio of from about 5 to 2 to about 13 to 0.01. Preferably, the vitamin E and the enzyme are in a weight ratio of about 10 to 1.

According to one embodiment, the inventive composition includes a chelating agent, which acts as an identifier of the plaque formation on the substrate and assists the enzyme in acting on or dissolving the plaque formation. The chelating agent may be present in an amount of from about 0.001 to about 2.5 weight percent of the composition.

Examples of chelating agents which are effective in the inventive composition are citric acid, ethylenediaminetetraacetic acid (EDTA) and the like. Preferably, the chelating agent is citric acid, present in an amount of from about 0.001 to about 2.5 weight percent of the composition, and preferably, present in an amount of from about 0.05 to about 1 weight percent of the composition.

According to another embodiment, the inventive composition includes either a catalyst or a promoter of the enzyme, which modifies the rate of the enzymatic reaction. Preferably, the rate of reaction is increased by the catalyst or promoter, such that effective results are achieved in a short amount of time, as in a typical user's brushing cycle of about thirty seconds. The catalyst or promoter may be present in an amount of from about 0.001 to about 0.35 weight percent of the composition.

Examples of effective promoters are zinc, selenium and the like. The preferred promoter is zinc, present in an amount of from about 0.0001 to about 0.35 weight percent of the composition, and preferably, present in an amount of about 0.001 weight percent of the composition.

The inventive composition is preferably a substantially anhydrous oil-based composition which includes an enzyme component and vitamin E in a localizing admixture, as well as a chelating agent and a promoter of the enzyme, all as described herein.

The inventive composition may include other additives, such as a dispersing agent which actively distributes the components of the composition in the oral cavity. The dispersing agent may be present in an amount of from about 3 to about 15 weight percent of the composition.

Examples of effective dispersing agents are AC-DI-SOL, available from FMC Corporation of Philadelphia, Pa., sodium bicarbonate and the like. Preferably, the dispersing agent is AC-DI-SOL, which includes croscarmellose sodium, sodium chloride and sodium glycolate. The AC-DI-SOL additive may be present in an amount of from about 3 to about 15 weight percent of the composition, and preferably, is present in an amount of about 6.9 weight percent.

Additionally, the inventive composition may include a thickening agent. Thickening agents such as gum compositions are insufficient, as either they are not sufficiently compatible with the vitamin E and enzyme components of the composition or they do not render the admixture of these components sufficiently resistant to dilution and wash-away in the presence of saliva. A preferred thickening agent is polyethylene glycol which is compatible with the vitamin E and enzyme components and provides a smooth feeling in the mouth. The polyethylene glycol additive also enhances the performance of the composition, as it reduces the solubility of the vitamin E and enzyme admixture in the mouth and thus, enhances the action of the enzyme in this localized admixture on the plaque-prone substrate.

Other possible additives include surfactants, such as sodium lauryl sulfate; abrasives, such as SYLOID, a silica product available from E. T. Horn of La Mirada, Calif.; smoothing and texturing agents, such as the polyethylene glycol additive described above; body-enhancing agents, such as methylcellulose, or METHOCEL, available from Van Waters and Rogers of Los Angeles, California, and including methoxyl, iron and sodium chloride; breath freshener agents, such as chlorophyll; sweetening agents, such as saccharin or NUTRASWEET available from The NutraSweet Company of Deerfield, Ill.; and flavoring or taste-enhancing agents or oils, such as wintergreen, spearmint, peppermint, cinnamon or clove oils. Such additives are chosen to provide the most pleasing taste, texture, and color of the composition, as well as the most effective surfactant and abrasive activity for the dentifrice composition. Additional additives may include desensitizing agents, whitening agents, active oxygen compounds, fluoride compounds and the like.

According to other aspects of the invention, the composition is provided in a variety of forms suitable for oral use and application. For example, the inventive composition may be encapsulated or tableted to form an edible capsule or tablet, impregnated in a dental floss or permeating at least an outer surface of a dental floss, added to a chewing medium, such as a gum, or provided in powder form, such as in a powder to be used by dental professionals for patients' dental cleanings.

EXAMPLES

Twelve oil-based, anti-plaque embodiments in accordance with the present invention were prepared, the inventive compositions including the components listed below in Table 1. Table 1 shows the component amounts in milligrams, unless otherwise specified.

TABLE 1

| Inventive Composition 1 | |
|---|---|
| COMPONENT | AMOUNT |
| Vitamin E | 55.0 |
| Pancreatin | 4.5 |
| Zinc Gluconate | 0.5 |
| Citric Acid | 3.0 |
| SYLOID | 20.0 |
| METHOCEL | 52.0 |
| AC-DI-SOL | 32.0 |
| Sodium Lauryl Sulfate | 28.0 |
| NUTRASWEET | 5.0 |
| Polyethylene Glycol | 250.0 |
| Sodium Fluoride | 2.0 |
| Chlorophyll | 0.45 |
| Magnesium Stearate | 6.0 |
| Wintergreen Oil | 4.0 ml |
| Spearmint Oil | 3.0 ml |
| Peppermint Oil | 1.5 ml |
| Inventive Composition 2 | |
| Vitamin E | 25.0 |
| Pancreatin | 0.05 |
| Zinc Gluconate | 0.0005 |
| Citric Acid | 0.005 |

TABLE 1-continued

| | |
|---|---|
| SYLOID | 40.0 |
| METHOCEL | 70.0 |
| AC-DI-SOL | 15.0 |
| Sodium Lauryl Sulfate | 15.0 |
| NUTRASWEET | 9.0 |
| Polyethylene Glycol | 290.0 |
| Sodium Fluoride | 5.0 |
| Chlorophyll | 1.0 |
| Magnesium Stearate | 2.0 |
| Wintergreen Oil | 1.5 ml |
| Spearmint Oil | 3.0 ml |
| Peppermint Oil | 4.0 ml |
| Inventive Composition 3 | |
| Vitamin E | 150.0 |
| Pancreatin | 60.0 |
| Zinc Gluconate | 5.0 |
| Citric Acid | 12.5 |
| SYLOID | 10.0 |
| METHOCEL | 22.0 |
| Sodium Lauryl Sulfate | 38.0 |
| AC-DI-SOL | 72.0 |
| NUTRASWEET | 1.0 |
| Polyethylene Glycol | 150.0 |
| Sodium Fluoride | 1.0 |
| Chlorophyll | 0.15 |
| Magnesium Stearate | 1.0 |
| Wintergreen Oil | 1.0 ml |
| Spearmint Oil | 2.0 ml |
| Peppermint Oil | 4.5 ml |
| Inventive Composition 4 | |
| Vitamin E | 20.0 |
| Papain | 0.05 |
| Zinc Gluconate | 0.005 |
| EDTA | 0.05 |
| Aluminum Hydrate | 40.0 |
| METHOCEL | 60.0 |
| Sodium Lauryl Sulfate | 20.0 |
| AC-DI-SOL | 40.0 |
| NUTRASWEET | 1.0 |
| Polyethylene Glycol | 200.0 |
| Sodium Fluoride | 1.5 |
| Magnesium Stearate | 3.0 |
| Spearmint Oil | 1 ml |
| Peppermint Oil | 3 ml |
| Cinnamon Oil | 2 ml |
| Inventive Composition 5 | |
| Vitamin E | 30.0 |
| EDTA | 3.0 |
| Zinc Gluconate | 0.5 |
| Papain | 4.5 |
| AC-DI-SOL | 30.0 |
| SYLOID | 25.0 |
| Sodium Alginate | 50.0 |
| Sodium Lauryl Sulfate | 25.0 |
| Saccharin | 2.0 |
| Polyethylene Glycol | 230.0 |
| Stannous Fluoride | 1.0 |
| Magnesium Stearate | 4.0 |
| Peppermint Oil | 4.0 ml |
| Clove Oil | 3.0 ml |
| Inventive Composition 6 | |
| Vitamin E | 60.0 |
| EDTA | 0.005 |
| Zinc Gluconate | 0.0005 |
| Papain | 0.05 |
| AC-DI-SOL | 15.0 |
| Dextranase | 3.0 |
| Sodium Alginate | 70.0 |
| Sodium Lauryl Sulfate | 15.0 |
| Saccharin | 9.0 |
| Polyethylene Glycol | 290.0 |
| Stannous Fluoride | 2.0 |
| Magnesium Stearate | 5.0 |
| SYLOID | 40.0 |
| Clove Oil | 1 ml |

TABLE 1-continued

| | |
|---|---|
| Peppermint Oil | 3 ml |
| Inventive Composition 7 | |
| Vitamin E | 95.0 |
| Dextranase | 4.5 |
| Glycerol Ester Hydrolase | 1.5 |
| Citric Acid | 3.0 |
| SYLOID | 20.0 |
| METHOCEL | 52.0 |
| AC-DI-SOL | 32.0 |
| Sodium Lauryl Sulfate | 28.0 |
| Zinc Gluconate | 0.5 |
| Polyethylene Glycol | 250.0 |
| Sodium Fluoride | 2.0 |
| Chlorophyll | 0.45 |
| Magnesium Stearate | 6.0 |
| Wintergreen Oil | 4.0 ml |
| Spearmint Oil | 3.0 ml |
| Peppermint Oil | 1.5 ml |
| Strontium Chloride Hexahydrate | 90.0 |
| Inventive Composition 8 | |
| Vitamin E | 25.0 |
| Glycerol Ester Hydrolase | 3.5 |
| Zinc Gluconate | 0.0005 |
| Citric Acid | 0.005 |
| SYLOID | 40.0 |
| METHOCEL | 70.0 |
| AC-DI-SOL | 15.0 |
| Sodium Lauryl Sulfate | 15.0 |
| Coconut Acid Ester of Sodium | 8.0 |
| Polyethylene Glycol | 290.0 |
| Sodium Fluoride | 5.0 |
| Chlorophyll | 1.0 |
| Magnesium Stearate | 2.0 |
| Wintergreen Oil | 1.5 ml |
| Spearmint Oil | 3.0 ml |
| Peppermint Oil | 4.0 ml |
| Strontium Chloride Hexahydrate | 25.0 |
| Inventive Composition 9 | |
| Vitamin E | 25.0 |
| Pancreatin | 2.5 |
| Zinc Gluconate | 1.5 |
| Citric Acid | 3.0 |
| SYLOID | 20.0 |
| METHOCEL | 52.0 |
| Potassium Nitrate | 5.0 |
| AC-DI-SOL | 32.0 |
| Sodium Lauryl Sulfate | 28.0 |
| NUTRASWEET | 5.0 |
| Polyethylene Glycol | 250.0 |
| Sodium Fluoride | 2.0 |
| Chlorophyll | 0.45 |
| Magnesium Stearate | 6.0 |
| Peppermint Oil | 1.5 ml |
| Wintergreen Oil | 4.0 ml |
| Spearmint Oil | 3.0 ml |
| Inventive Composition 10 | |
| Vitamin E | 15.0 |
| Pancreatin | 0.5 |
| Zinc Gluconate | 0.0005 |
| Citric Acid | 0.005 |
| SYLOID | 40.0 |
| Myristic Acid-2-Sulfoethyl Ester, Sodium Salt | 8.5 |
| AC-DI-SOL | 15.0 |
| Sodium Lauryl Sulfate | 1.0 |
| NUTRASWEET | 9.0 |
| Polyethylene Glycol | 290.0 |
| Sodium Fluoride | 5.0 |
| Chlorophyll | 1.0 |
| Magnesium Stearate | 2.0 |
| Potassium Nitrate | 50.0 |

TABLE 1-continued

| | |
|---|---|
| Wintergreen Oil | 1.5 ml |
| Spearmint Oil | 2.0 ml |
| Peppermint Oil | 4.0 ml |
| Inventive Composition 11 | |
| Vitamin E | 45.0 |
| Phospholipases | 4.5 |
| Zinc Gluconate | 0.5 |
| Citric Acid | 3.0 |
| SYLOID | 20.0 |
| METHOCEL | 52.0 |
| AC-DI-SOL | 32.0 |
| Sodium Lauryl Sulfate | 28.0 |
| NUTRASWEET | 5.0 |
| Polyethylene Glycol | 250.0 |
| Stannous Fluoride | 2.0 |
| Chlorophyll | 0.45 |
| Magnesium Stearate | 6.0 |
| Sodium Monofluorophosphate | 2.5 |
| Wintergreen Oil | 4.0 ml |
| Spearmint Oil | 3.0 ml |
| Peppermint Oil | 1.5 ml |
| Inventive Composition 12 | |
| Vitamin E | 65.0 |
| Pancreatin | 0.05 |
| Zinc Gluconate | 0.0005 |
| Citric Acid | 0.005 |
| SYLOID | 40.0 |
| METHOCEL | 70.0 |
| AC-DI-SOL | 15.0 |
| Sodium Lauryl Sulfate | 15.0 |
| NUTRASWEET | 9.0 |
| Polyethylene Glycol | 290.0 |
| Sodium Fluoride | 1.0 |
| Chlorophyll | 1.0 |
| Magnesium Stearate | 2.0 |
| Sodium Monofluorophosphate | 8.0 |
| POLOXAMER 407 | 10.0 |
| Spearmint Oil | 3.0 ml |
| Peppermint Oil | 3.0 ml |

In Composition 12, the POLOXAMER 407 is a non-ionic surfactant available from Parsippany, New Jersey, and may be replaced by PLURONIC 127, a non-ionic surfactant available from the same source.

A first composition, namely, Inventive Composition 1 shown in Table 1, was formulated in the tablet form described above. This first composition was given to a first group of twelve patients who were instructed to use the tablets instead of toothpaste and to floss once daily.

A second (control) composition was similarly formulated; however, this second composition included the vitamin E component, but none of the other components listed in Table 1. This second composition was given to a second group of twelve patients who were instructed in the same manner as those in the first group.

A similarly formulated third (control) composition included neither the vitamin E component nor the other components listed in Table 1. This third composition was given to a third group of twelve patients who were instructed in the same manner as those in the first and second groups.

After sixty days, the thirty-six patients were examined for gingival and dental health and tested using a standard erythrocin dye. The patients in the first group not only showed the most gingival improvement, but also exhibited almost no plaque. In the second group, nine of the patients showed gingival improvement, but all of the patients exhibited more plaque on the posterior teeth than did those in the first group. In the third group, six patients showed gingival improvement, but all of the patients exhibited plaque on both the anterior and posterior teeth. The improvement in the gingival health of the third group is believed to be primarily a result of better oral hygiene during the test period, perhaps induced by the patients' behavioral response to knowledge of examination and testing following the test period.

The results of the examination and testing performed on the thirty-six patients evidence a dramatic improvement in the gingival and dental health of the patients in the first group who used the inventive composition. Further, the almost complete lack of dental plaque exhibited by the patients in the first group, as compared to that exhibited by those in the second group, evidence that the inventive compositions are more effective than a composition including vitamin E alone.

Patients using the inventive compositions have reported their experience of a slippery clean feeling on their teeth after use, a feeling they had not previously experienced when using other dentifrices. It is believed that this clean feeling is a result of both the absence of plaque and the presence of a prophylactic coating on the teeth which prevents the formation of new plaque.

In summary, the preferred dentifrice compositions, including an enzyme and vitamin E which form a highly effective localizing admixture, result in a unique product for oral heath care.

It is to be understood that while the invention has been described above in conjunction with preferred specific embodiments, the description is intended to illustrate and not to limit the scope of the invention, which is defined by the scope of the appended claims.

Iit is claimed:

1. An oil-based, anti-plaque composition for use in an oral cavity, consisting essentially of:
   at least one enzyme selected from the group consisting of proteases, lipases and saccharinases; and
   vitamin E, the vitamin E and the enzyme forming a localizing admixture for an oral substrate contacted therewith, the admixture having the vitamin E and the enzyme in a weight ratio of from about 5:2 to about 13:0.01.

2. The composition of claim 1 wherein said composition is substantially anhydrous.

3. The composition of claim 2 wherein the enzyme is derived from the group consisting of pancreatin, trypsin, papain, collagenase, keratinase, carboxylase, aminopeptidase, lactate dehydrogenase and glucosyltransferase.

4. The composition of claim 2 wherein said vitamin E is selected from the group consisting of α-tocopheryl acetate and α-tocopheryl succinate.

5. The composition of claim 2, further comprising a chelating agent.

6. The composition of claim 5 wherein the chelating agent includes citric acid or ethylenediaminetetraacetic acid.

7. The composition of claim 2, further comprising a promoter of the enzyme.

8. The composition of claim 7 wherein the promoter includes zinc or selenium.

9. A substantially anhydrous oil-based, anti-plaque composition for use in an oral cavity, consisting essentially of:
   at least one enzyme selected from the group consisting of proteases, lipases and saccharinases;
   vitamin E, the vitamin E and the enzyme forming a localizing admixture for an oral substrate contacted therewith;
   a chelating agent; and
   a promoter of the enzyme.

10. The composition of claim 9 wherein the enzyme is derived from the group consisting of pancreatin, trypsin, papain, collagenase, keratinase, carboxylase, aminopeptidase, lactate dehydrogenase and glucosyltransferase.

11. The composition of claim 9 wherein said vitamin E is selected from the group consisting of α-tocopheryl acetate and α-tocopheryl succinate.

12. The composition of claim 9 wherein the chelating agent includes citric acid or ethylenediaminetetraacetic acid.

13. The composition of claim 9 wherein the promoter includes zinc or selenium.

14. The composition of any one of claims 2 and 9 in a powder form.

* * * * *